United States Patent [19]

Kim et al.

[11] Patent Number: 4,497,952
[45] Date of Patent: Feb. 5, 1985

[54] PROCESS FOR THE PRODUCTION OF (±)-4-OXO-1,2,3,6,7,11b-HEXAHYDRO-4H-PYRAZINO[2,1-A]ISOQUINOLINE DERIVATIVES

[75] Inventors: Choong S. Kim; Nam J. Lee; Joong H. Kim, all of Seoul, Rep. of Korea

[73] Assignee: Korea Advanced Institute of Science and Technology, Seoul, Rep. of Korea

[21] Appl. No.: 511,999

[22] Filed: Jul. 8, 1983

[30] Foreign Application Priority Data

Jul. 8, 1982 [KR] Rep. of Korea .................. 1982-3036
May 30, 1983 [KR] Rep. of Korea .................. 1983-2413

[51] Int. Cl.³ .................. C07D 471/04; C07D 241/08
[52] U.S. Cl. .................. 544/344; 544/385; 544/406
[58] Field of Search .................. 544/344, 408, 385; 546/95

[56] References Cited

U.S. PATENT DOCUMENTS

| | | | |
|---|---|---|---|
| 2,763,652 | 9/1956 | Sapir et al. | 544/385 |
| 2,927,114 | 3/1960 | Izzo et al. | 544/385 |
| 3,502,679 | 3/1970 | Honlihan et al. | 546/95 |
| 3,993,760 | 11/1976 | Pohlke et al. | 424/250 |

FOREIGN PATENT DOCUMENTS

| | | |
|---|---|---|
| 1511463 | 5/1978 | European Pat. Off. |
| 2457971 | 10/1976 | Fed. Rep. of Germany |
| 3006478 | 9/1981 | Fed. Rep. of Germany |
| 0429351 | 11/1967 | Japan |

OTHER PUBLICATIONS

Hubert et al., Tetrahedron Letters 44, 4493–4496 (1972).
Lal et al., Chem. Abst. 96, 35289 (1982).

Primary Examiner—Mark L. Berch
Attorney, Agent, or Firm—Birch, Stewart, Kolasch & Birch

[57] ABSTRACT

This invention discloses a process for the preparation of (±)-4-oxo-1,2,3,6,7,11b-hexahydro-4H-pyrazino[2,1-a]isoquinoline derivatives which comprises conducting an intramolecular cyclization reaction of the compounds of formulas II III in an acid medium.

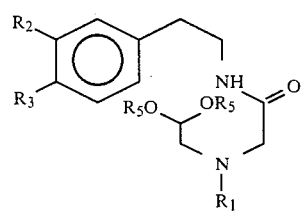

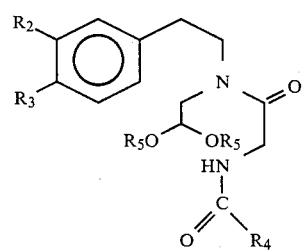

13 Claims, No Drawings

PROCESS FOR THE PRODUCTION OF (±)-4-OXO-1,2,3,6,7,11B-HEXAHYDRO-4H-PYRAZINO[2,1-A]ISOQUINOLINE DERIVATIVES

The present invention relates to a new and improved process for the preparation of (±)-4-oxo-1,2,3,6,7,11b-hexahydro-4H-pyrazino-4H-pyrazino[2,1-a]isoquinoline derivatives.

The compounds of the present invention are represented by the following general structural formula I:

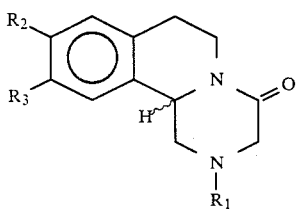

wherein $R_1$ is hydrogen, a loweralkyl or $R_4CO$ ; and $R_2$ and $R_3$ are independently hydrogen, a loweralkyl and alkoxy; and $R_4$ is hydrogen, a loweralkyl, cycloalkyl or aryl.

As used herein the term "loweralkyl" means a straight or branched chain $C_1$-$C_6$ alkyl.

The term "alkoxy" means a straight or branched chain $C_1$-$C_6$ alkoxy.

The term "cycloalkyl" means a cycloalkyl having 3 to 6 membered ring (e.g., cyclopropyl, cyclobutyl, cyclopentyl, cyclohexyl and the like).

The term "aryl" means phenyl or a phenyl optionally substituted by one or more radicals selected from the group consisting of a $C_1$-$C_6$ alkyl, halogen, nitro or $C_1$-$C_6$ alkoxy.

Certain compounds of formula I are known compounds or exhibit anthelmintic activity against schistosomes.

The compounds of formula I described herein have been prepared by various methods known to the prior art.

In one prior art process described in U.S. Pat. No. 3,993,760 (1976), the compounds of formula I are prepared by cyclization of 1-(N-acylaminomethyl)-2-halomethylcarboxy-1,2,3,4-tetrahydroisoquinoline.

Similar and other processes are also described in DOS Nos. 2,457,971 (1976) and 2,504,250 (1976) and Experientia 33, 1036 (1977).

The prior art processes described in above literatures have certain inherent disadvantages. For instance, the process disclosed in U.S. Pat. No. 3,993,760 (1976) requires high pressure catalytic hydrogenation at high temperature (~100° C.) to produce the starting material, 1-aminomethyl-1,2,3,4-tetrahydroisoquinoline, from 1-cyano-2-acyl-1,2,-dihydroisoquinoline. Other processes described in DOS Nos. 2,457,971 and 2,504,250 (1976) and Experientia 33, 1036 (1977) are not economically attractive for industrial application.

It is therefore an object of the present invention to overcome these disadvantages associated with the prior art processes.

It is another object of this invention to provide a simple and economical process for the production of the compound of formula I in large scale.

The present invention relates to the discovery of a novel process for the preparation of the compounds of formula I, which comprises conducting an intramolecular cyclization reaction of the compounds represented by the following structural formulas II or III:

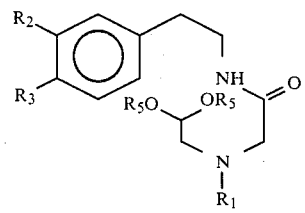

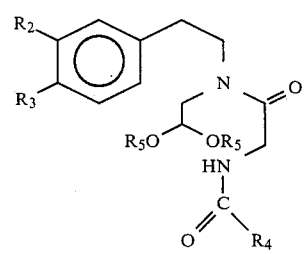

wherein $R_1$, $R_2$, $R_3$ and $R_4$ are as defined above and $R_5$ is methyl, ethyl or both $R_5$ groups together form a methylene group.

The important novelty of this invention is to form isoquinoline and piperazine ring simultaneously or stepwise by an intramolecular cyclization reaction.

In accordance with the process of the present invention, the compounds of formula II, wherein $R_1$ is an acyl substituent, can be converted into the compounds of formula I directly or, if desired, via the intermediates of formula IV or V, below, which can be isolated under certain reaction conditions.

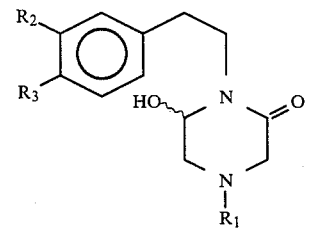

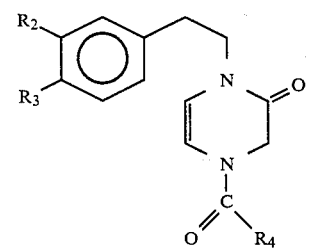

The compounds of formula III also can be converted to the compounds of formula I directly or via the intermediates of formula V.

The process of the present invention is expediently carried out in an acid medium. An excess of the acid can be used as solvent or the reaction can be carried out in the presence of an organic solvent.

Suitable acids for use in the process of the present invention include sulfuric acid, hydrochloric acid, phosphoric acid, polyphosphoric acid (PPA), formic acid, acetic acid, trichloroacetic acid, trifluoroacetic acid, methanesulfonic acid, p-toluenesulfonic acid and boron trifluoride etherate.

Suitable organic solvents include dichloromethane, chloroform, carbontetrachloride, 1,2-dichloroethane, methanol, ethanol, isopropanol, 1,4-dioxane, tetrahydrofuran (THF), diethyl ether, ethylene glycol, dimethyl ether and acetonitrile.

The one-step conversion of the compounds of formula II or III into the compounds of formula I is preferably carried out in a strong acid medium without solvent at a temperature from 20° C. to 40° C. Concentrated sulfuric acid or methansulfonic acid is prefered. The reaction is usually complete in about 2 to 8 hours.

In the two-step case when the cyclization reaction of the compounds of formula II or III is carried out in the presence of catalytic amount of an acid with an organic solvent as hereinabove mentioned the compounds of formula V are isolated in excellent yield.

Also, the compounds of formula IV are isolated when the compound of formula II, wherein R is an acyl substituent, is treated with a strong acid at low temperature, preferable at 10° C. to 20° C. for about 30 minutes, and then added to an aqueous alkaline medium.

The further cyclization reaction of the compounds of formula IV or V to the compounds of formula I is carried out in a strong acid medium as previously mentioned in the preparation of the compound formula I from the compounds of formula II or III. Usually the reaction is carried out without solvent at about room temperature.

The intramolecular cyclization reaction in this invention can be theoretically supported by the similar reaction described in the literatures [Tet. Let. No. 44, 4493 (1972) and ibid, No.11, 935 (1977)].

The compound of formula I wherein $R_1$ is an acyl substituent can be prepared by acylation of the compound of formula I, wherein $R_1$ is hydrogen, with a corresponding acylchloride or an acid anhydride.

The starting material, the compound of formula II, may be prepared by simply reacting N-(2-phenyl)ethyl-monochloroacetamide [JACS 55, 2555 (1933)] with N-substituted or unsubstituted aminoacetaldehyde dialkylacetal.

The compound of formula III may be prepared by treating the N-(2,2-dialkoxy)ethylphenethylamine (prepared from phenethylamine and chloro or bromoacetaldehyde dialkylacetal) with N-acylglycine.

The following examples further illustrate the present invention, but they are not constructed to limit the scope of the invention.

EXAMPLE 1

($\pm$)-4-oxo-1,2,3,6,7,11b-hexahydro-4H-pyrazino[2,1-a]isoquinoline (I; $R_1=R_2=R_3=H$)

22.6 g of N-(2-phenyl)ethyl-α-N-(2,2-dimethoxy)ethylglycine amide (II; $R_1=R_2=R_3=H$, $R_5=CH_3$) was added to 40 ml of concentrated sulfuric acid with cooling. The mixture was stirred at room temperature for 3 hours. After completion of the reaction, the resultant mixture was poured into ice-water, and then neutralized with ~20% aqueous sodium hydroxide with cooling. The neutralized solution was extracted with diethyl ether, and the ether extract was concentrated to give 12.3 g (61%) of the product, m.p. 118°~120° C.

EXAMPLE 2

($\pm$)-4-oxo-1,2,3,6,7,11b-hexahydro-4H-pyrazino[2,1-a]isoquinoline (I; $R_1=R_2=R_3=H$)

To a mixture of 10 ml of concentrated sulfuric acid and 5 ml of acetonitrile was added 2.7 g of N-(2-phenyl)ethyl-α-N-(2,2-dimethoxy)ethylglycine amide (II; $R_1=R_2=R_3=H$, $R_5=CH_3$). The resultant mixture was stirred at room temperature for 5 hours. The reaction mixture was worked up by the same procedure as in Example 1 to give 1.8 g (89%) of the product.

When diethyl ether is used as solvent instead of the acetonitrile, the reaction gives the same result.

EXAMPLE 3

($\pm$)-2-cyclohexanecarbonyl-4-oxo-1,2,3,6,7,11b-hexahydro-4H-pyrazino[2,1-a]isoquinoline (I; $R_1$=cyclohexanecarbonyl, $R_2=R_3=H$)

3.76 g (0.01 mol) of N-(2-phenyl)ethyl-α-[N-(2,2-dimethoxy)ethyl-N-cyclohexanecarbonyl]glycine amide (II; $R_1$=cyclohexanecarbonyl, $R_2=R_3=H$, $R_5$=methyl) was added to 20 ml of methanesulfonic acid and the resultant mixture was stirred at room temperature for 8 hours. The reaction mixture was concentrated in vacuo, and then the residue was diluted with water and neutralized with ~10% aqueous sodium hydroxide solution. The neutralized solution was extracted with dichloromethane, and the extract was concentrated. The residue was recrystallized with ethyl acetate to give 1.9 g (61%) of the product, m.p. 133°~134° C.

EXAMPLE 4

($\pm$)-2-benzoyl-4-oxo-1,2,3,6,7,11b-hexahydro-4H-pyrazino[2,1-a]isoquinoline (I; $R_1$=benzoyl, $R_2=R_3=H$)

A solution of 3.7 g of N-(2-phenyl)ethyl-α-[N-(2,2-dimethoxy)ethyl-N-benzoyl]glycine amide in 5 ml of diethyl ether was added slowly to 10 ml of concentrated sulfuric acid. The mixture was stirred at room temperature for 7 hours. After completion of the reaction, the resultant mixture was poured into ice-water and neutralized with aqueous alkali. The resultant solution was extracted with diethyl ether, and then the ether extract was concentrated. The residue was recrystallized with ethyl acetate to give 1.8 g (68%) of the product, m.p. 162°~163° C.

EXAMPLE 5

1-(2-phenyl)ethyl-4-acetyl-2-hydroxypiperazine-6-one (IV; $R_1$=acetyl, $R_2=R_3=H$)

To 5 ml of concentrated sulfuric acid was added 3.08 g of N-(2-phenyl)ethyl-α-[N-(2,2-dimethyoxy)ethyl-N-acetyl]glycine amide (II; $R_1$=acetyl, $R_2=R_3=H$, $R_5$=methyl). The mixture was stirred at room temperature for 30 minutes. The reaction mixture was slowly added to ~10% aqueous sodium hydroxide solution with cooling. The resultant mixture was extracted with dichloromethane, and then the extract was concentrated. The residue was recrystallized with ethyl acetate-hexane to give the 2.4 g (92%) of the product, m.p. 128°~129° C. nmr(CDCl$_3$)δ: 2.05(s,3,COCH$_3$), 2.65-4.80(m,10, CH$_2$, CH), 7.20(s,5, phenyl ring portions), IR(KBr)cm$^{-1}$: 3350(s,OH), 2930(m, CH), 1650(s, CO), 1420–1480(s), 1170(s)

EXAMPLE 6

1-(2-phenyl)ethyl-4-cyclohexanecarbonyl-2,3-dehydropiperazine-6-one (V; R$_4$=cyclohexyl, R$_2$=R$_3$=H)

To a solution of 4.0 g of N-(2-phenyl)ethyl-N-(2,2-diethoxy)ethyl-α-N-cyclohexanecarbonylglycine amide (III; R$_4$=cyclohexyl, R$_2$=R$_3$=H, R$_5$=ethyl) in 10 ml of dichloromethane was added 1 ml of methanesulfonic acid. The mixture was stirred at room temperature for 3 hours. The reaction mixture was washed with aqueous alkaline solution, and then the organic layer was concentrated. The residue was recrystallized with ethyl acetate-hexane to give 2.8 g (90%) of the product, m.p. 128°~130° C. nmr(CDCl$_3$)δ: 0.85–2.0(m, 10, cyclohexane ring protons), 2.90(t, 2, CH$_2$), 3.70(t, 2, CH$_2$), 4.20(s, 2, CH$_2$), 5.30(d, 1, vinyl proton), 6.00(d, 1, vinyl proton), 7.10(s, t, phenyl ring protons), IR(KBr)cm$^{-1}$: 2930(m, CH), 1660(s, CO), 1450, 1400(m), 1300(m), 1000(m), 700(w).

EXAMPLE 7

(±)-2-cyclohexanecarbonyl-4-oxo-1,2,3,6,7,11b-hexahydro-4H-pyrazino[2,1-a]isoquinoline (I; R$_1$=cyclohexanecarbonyl, R$_2$=R$_3$=H)

3.3 g of 1-(2-phenyl)ethyl-4-cyclohexanecarbonyl-2-hydroxypiperazine-6-one (V; R$_2$=R$_3$=H, R$_1$=cyclohexanecarbonyl) was slowly added to 5 ml of concentrated sulfuric acid. The mixture was stirred at room temperature for 3 hours. The reaction mixture was poured into ice-water and neutralized with aqueous alkali. The resultant mixture was extracted with dichloromethane, and then the extract was concentrated. The residue was recrystallized with ethyl acetate to give 3.0 g (95%) of the product, m.p. 132°~134° C.

EXAMPLE 8

(±)-2-acetyl-4-oxo-1,2,3,6,7,11b-hexahydro-4H-pyrazino[2,1-a]isoquinoline (I; R$_1$=acetyl, R$_2$=R$_3$=H)

To a solution of 3.4 g of N-(2-phenyl)ethyl-N-(2,2-diethoxy)ethyl-α-N-acetylglycine amide (III; R$_2$=R$_3$=H, R$_4$=methyl) in 10 ml of 1,2-dichloroethane was added 3 ml of methanesulfonic acid. The mixture was refluxed for 8 hours. After completion of the reaction, the resultant mixture was washed with aqueous alkali, and then the organic layer was concentrated. The residue was recrystallized with ethyl acetate to give 2.1 g (86%) of the product, m.p. 144°~145° C.

EXAMPLE 9

1-(2-phenyl)ethyl-4-cyclohexanecarbonyl-2,3-dehydropiperazin-6-one (V; R$_2$=R$_3$=H, R$_4$=cyclohexyl)

3.8 g of N-(2-phenyl)ethyl-α-[N-(2,2-dimethoxy)ethyl-N cyclohexanecarbonyl]glycine amide (II; R$_1$=cyclohexanecarbonyl, R$_2$=R$_3$=H, R$_5$=methyl) was added to 5 ml of 20% hydrochloric acid, and then the mixture was stirred at room temperature for 3 hours. After completion of the reaction, the resultant solid was collected by filtration to give 2.9 g (93%) of the product, m.p. 129 131° C.

EXAMPLE 10

(±)-4-oxo-9,10-dimethoxy-1,2,3,6,7,11b-hexahydro-4H-pyrazino[2,1-a]isoquinoline (I; R$_1$=H, R$_2$=R$_3$=OCH$_3$)

2.16 g of N-[2-(3,4-dimethoxyphenyl)ethyl]-α-N-(2,2-dimethoxy)ethylglycine amide (II; R$_1$=H, R$_2$=R$_3$=OCH$_3$, R$_5$=CH$_3$) was added to 2 ml of concentrated sulfuric acid at 0° C. The mixture was stirred at room temperature for 1.5 hours. The resultant mixture was poured into ice-water and neutralized with aqueous alkali to PH=~8. The neutralized solution was extracted with dichloromethane, and then the extract was concentrated. The residue was recrystallized with ethyl acetate to give 1.5 g (96%) of product, m.p. 136°~137° C. nmr(CDCl$_3$)δ: 2.0(s,1, NH), 2.30~3.10(m, 4, CH$_2$), 3.30~4.00(m, 3, CH$_2$ and CH), 3.8(s, 6, OCH$_3$), 4.40~5.00(m, 2, CH$_2$), 6.5(s, 2, phenyl ring protons)

EXAMPLE 11

(±)-2-(p-chlorobenzoyl)-4-oxo-9,10-dimethyoxy-1,2,3,6,7,11b-hexahydro-4H-pyrazino[2,1-a]isoquinoline (I; R$_1$=p-chlorobenzoyl, R$_2$=R$_3$=OCH$_3$)

To a solution of 2.62 g of (±)-4-oxo-9,10-dimethoxy-1,2,3,6,7,11b-hexahydro-4H-pyrazino[2,1-a]isoquinoline (I; R$_1$=H, R$_2$=R$_2$=OCH$_3$) in 10 ml of dichloromethane was added 2 ml of triethylamine, and then 1.9 g of p-chlorobenzoyl chloride was slowly added 0°~5° C. The resultant mixture was stirred at 10° C. for 1.5 hours. To the reaction mixture was added water, and the organic layer was seperated. The organic extract was concentrated, and then the residue was triturated with ethyl acetate-ether to obtain 4.0 g (~100%) of the product, m.p. 139°~140° C.

EXAMPLE 12

N-[2-(3,4-dimethoxyphenyl)ethyl]-α-N-(2,2-dimethoxy)ehtylglycine amide (II, R$_1$=H, R$_2$=R$_3$=OCH$_3$)

12.86 g of N-(3,4-dimethoxyphenyl)ethylmonochloroacetamide and 11.6 g of aminoacetaldehyde dimethylacetal were added to 10 ml of toluene, and the mixture was refluxed for 40 minutes. After cooling the reaction mixture, the resultant solid was filtered off. The filtrate was washed with water, and then the toluene solution was concentrated to give a viscous oil (16.19 g, 99.3%), HCl salt m.p. 98°~99° C. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for the production of (±)-4-oxo-1,2,3,6,7,11b-hexahydro-4H-pyrazino[2,1-a]isoquinolines of formula I:

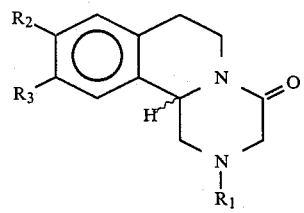

which comprises an intramolecular cyclization reaction of a compound of formula II or III, in an acid medium, wherein said acid is at least one member selected from the group consisting of sulfuric acid, hydrochloric acid, phosphoric acid, polyphosphoric acid (PPA), formic acid, acetic acid, trichloroacetic acid, trifluoroacetic acid, methanesulfonic acid, p-toluene-sulfonic acid and boron trifluoride etherate, with or without organic solvent,

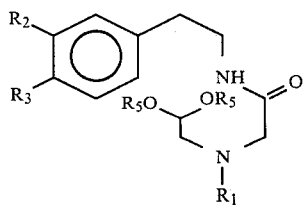

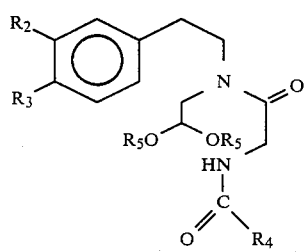

wherein $R_1$ represents hydrogen, a loweralkyl or $R_4CO$; $R_2$ and $R_3$ each independently represent hydrogen, a loweralkyl or alkoxy; $R_4$ represents hydrogen, a loweralkyl, cyclopropyl, cyclobutyl, cyclopentyl, cyclohexyl, phenyl or phenyl substituted by one or more of the radicals selected from the group consisting of $C_1-C_6$ alkyl, halogen, nitro and $C_1-C_6$ alkoxy, and $R_5$ represents methyl, ethyl or methylene.

2. The process according to claim 1 wherein said acid is selected from the group consisting of sulfuric acid, hydrochloric acid, phosphoric acid, polyphosphoric acid (PPA), formic acid, acetic acid, trichloroacetic acid, trifluoroacetic acid, methanesulfonic acid, p-toluene-sulfonic acid and boron trifluoride etherate.

3. The process according to claim 1 wherein when the organic solvent is present, said organic solvent is selected from the group consisting of dichloromethane, chloroform, carbontetrachloride, 1,2-dichloroethane, methanol, ethanol, isopropanol, 1,4-dioxane, tetrahydrofuran(THF), diethyl ether, ethylene glycol dimethyl ether and acetonitrile.

4. The process according to claim 1 wherein the cyclization reaction of the compounds of formula II, wherein $R_1$ is $R_4CO$, is effected in the presence of an acid and organic solvent by a two-step reaction via the intermediate compound of formula IV:

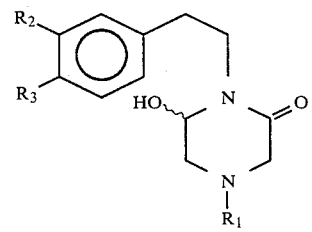

wherein $R_1$ represents $R_4CO$; and $R_2$ and $R_3$ independently represent hydrogen, a loweralkyl or alkoxy; and $R_4$ represents hydrogen, a loweralkyl, cyclopropyl, cyclobutyl, cyclopentyl, cyclohexyl, phenyl or phenyl substituted by one or more of the radicals selected from the group consisting of $C_1-C_6$ alkyl, halogen, nitro and $C_1-C_6$ alkoxy.

5. The process according in claim 1 wherein the cyclization reaction of the compounds of formula II or III are effected in the presence of an acid and organic solvent by a two-step reaction via the intermediate compound of formula V:

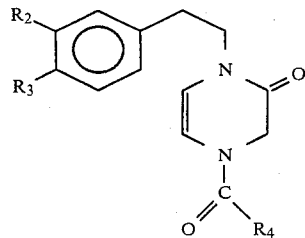

wherein $R_2$ and $R_3$ represent independently hydrogen, a loweralkyl, or alkoxy; and $R_4$ represents hydrogen, a loweralkyl cyclopropyl, cyclobutyl, cyclopentyl, cyclohexyl, phenyl or phenyl substituted by one or more of the radicals selected from the group consisting of $C_1-C_6$ alkyl, halogen, nitro and $C_1-C_6$ alkoxy.

6. The method of claim 1 wherein the conversion is effected without a solvent at a temperature of from 20°–40° C.

7. The method of claim 4 wherein the acid treatment of said compounds of formula II is effected at a temperature of 10°–20° C.

8. A process for the production of (±)-4-oxo-1,2,3,6,7,11b-hexahydro-4H-pyrazino[2,1-a]isoquinolines of formula I:

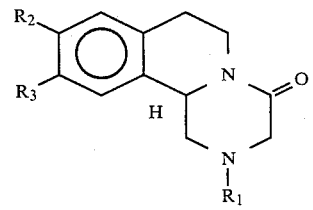

which comprises an intramolecular cyclization reaction of a compound of formula II, in an acid medium, wherein said acid is at least one member selected from the group consisting of sulfuric acid, hydrochloric acid, phosphoric acid, polyphosphoric acid (PPA), formic acid, acetic acid, trichloroacetic acid, trifluoroacetic acid, methanesulfonic acid, p-toluene-sulfonic acid and boron trifluoride etherate, with or without organic solvent,

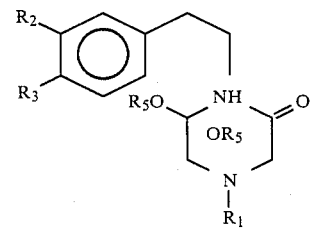

wherein $R_1$ represents hydrogen, a loweralkyl or $R_4CO$; $R_2$ and $R_3$ each independently represent hydrogen, a loweralkyl or alkoxy; $R_4$ represents hydrogen, a loweralkyl, cyclopropyl, cyclobutyl, cyclopentyl, cyclohexyl, phenyl or phenyl substituted by one or more of the radicals selected from the group consisting of $C_1$–$C_6$ alkyl, halogen, nitro and $C_1$–$C_6$ alkoxy, and $R_5$ represents methyl or ethyl or both $R_5$ groups together form a methylene group.

9. The process according to claim 8 wherein the cyclization reaction of the compounds of formula II is effected in the presence of an acid and organic solvent by a two-step reaction via the intermediate compound of formula V:

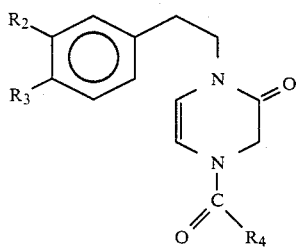

wherein $R_2$ and $R_3$ represent independently hydrogen, a loweralkyl, or alkoxy; and $R_4$ represents hydrogen, a loweralkyl, cyclopropyl, cyclobutyl, cyclopentyl, cyclohexyl, phenyl or phenyl substituted by one or more of the radicals selected from the group consisting of $C_1$–$C_6$ alkyl, halogen, nitro and $C_1$–$C_6$ alkoxy.

10. The process according to claim 8 wherein when the organic solvent is present, said organic solvent is selected from the group consisting of dichloromethane, chloroform, carbontetrachloride, 1,2-dichloroethane, methanol, ethanol, isopropanol, 1,4-dioxane, tetrahydrofuran (THF), diethyl ether ethylene glycol dimethyl ether and acetonitrile.

11. The process according to claim 8, wherein the cyclization reaction of the compounds of formula II wherein $R_1$ is $R_4CO$, is effected in the presence of an acid and organic solvent by a two-step reaction via the intermediate compound of formula IV:

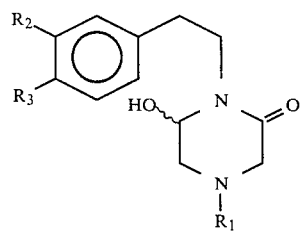

wherein $R_1$ represents $R_4CO$; and $R_2$ and $R_3$ independently represent hydrogen, a loweralkyl or alkoxy; and $R_4$ represents hydrogen, a loweralkyl, cyclopropyl, cyclobutyl, cyclopentyl, cyclohexyl, phenyl or phenyl substituted by one or more of the radicals selected from the group consisting of $C_1$–$C_6$ alkyl, halogen, nitro and $C_1$–$C_6$ alkoxy.

12. The method of claim 1, wherein said lower alkyl is a straight or branched chain $C_1$–$C_6$ alkyl and said alkoxy is a straight or branched chain $C_1$–$C_6$ alkoxy.

13. The method of claim 4, wherein said lower alkyl is a straight or branched chain $C_1$–$C_6$ alkyl and said alkoxy is a straight or branched chain $C_1$–$C_6$ alkoxy.

* * * * *